United States Patent [19]

Ahmad et al.

[11] Patent Number: 5,514,698
[45] Date of Patent: May 7, 1996

[54] ANTIFUNGAL VAGINAL CREAM COMPOSITION

[75] Inventors: Nawaz Ahmad, Monmouth Jct.;
Barbara Brummer, Upper Montclair;
Nandita M. Dalal, East Brunswick;
Rohinton Toddywala, North Brunswick, all of N.J.

[73] Assignee: Ortho Pharmaceutical Corporation, Raritan, N.J.

[21] Appl. No.: 216,215

[22] Filed: Mar. 21, 1994

[51] Int. Cl.$^6$ .............. A61K 9/06; A61K 9/113; A61K 31/415

[52] U.S. Cl. .............. 514/396; 514/397; 514/398; 514/399; 514/937; 514/938; 514/969

[58] Field of Search .............. 514/396–399, 514/938, 969

[56] References Cited

U.S. PATENT DOCUMENTS

| | | | |
|---|---|---|---|
| 4,048,310 | 9/1977 | Chen et al. | 424/238 |
| 4,267,169 | 5/1981 | Kamishita et al. | 424/273 |
| 4,446,145 | 5/1984 | Van Bever | 424/273 |
| 4,775,678 | 10/1988 | Su et al. | 514/396 |
| 4,883,792 | 11/1989 | Timmins et al. | 514/399 |
| 4,911,932 | 3/1990 | Clum et al. | 424/642 |
| 4,912,124 | 3/1990 | Das et al. | 514/399 |
| 5,002,938 | 3/1991 | Wang et al. | 514/399 |
| 5,087,620 | 2/1992 | Parab | 514/399 |
| 5,110,809 | 5/1992 | Wang et al. | 514/399 |
| 5,208,015 | 5/1993 | Shah et al. | 514/396 |
| 5,219,877 | 6/1993 | Shah et al. | 514/399 |
| 5,374,633 | 12/1994 | Parab | 514/252 |

*Primary Examiner*—Shep K. Rose

[57] ABSTRACT

A long-lasting antifungal vaginal cream composition having stable viscosity at human body temperature is disclosed.

19 Claims, 8 Drawing Sheets

FIG. 1 CREAM OF EXAMPLE 1 VISCOSITY AT 25°C
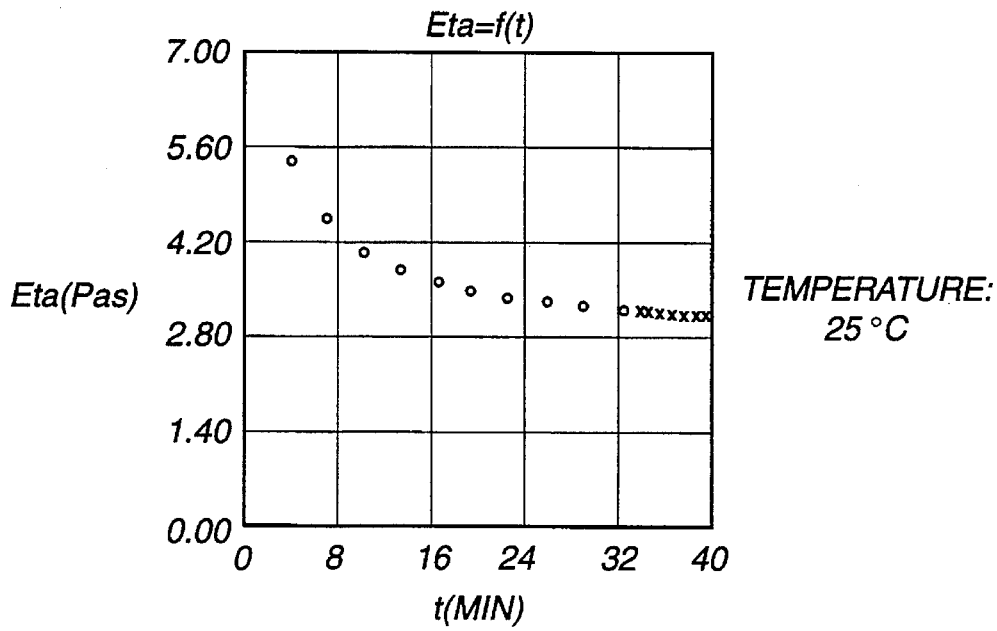
FIG. 2 CREAM OF EXAMPLE 1 VISCOSITY AT 37°C
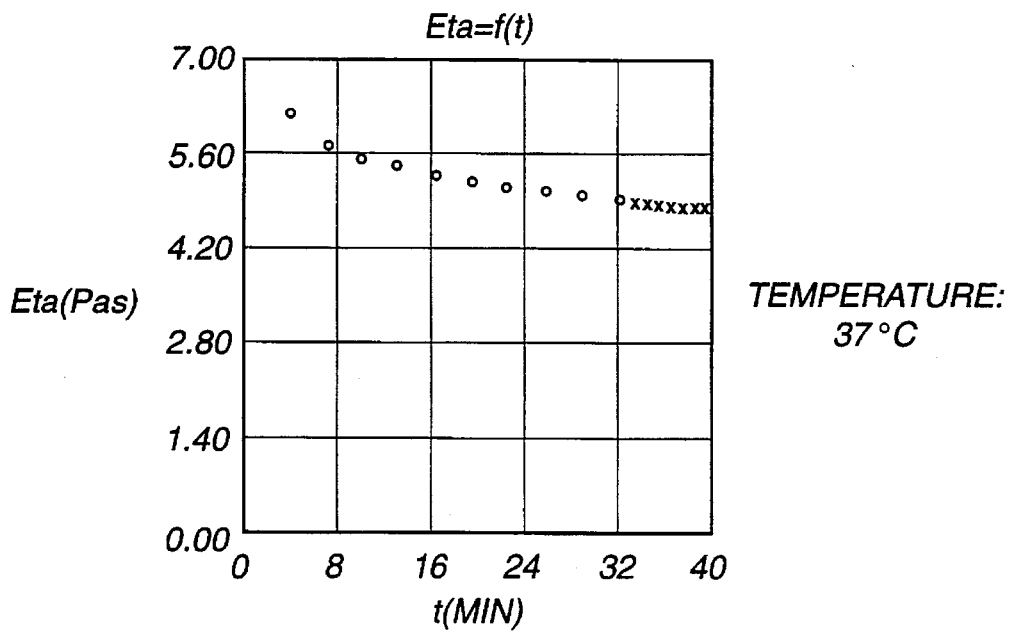

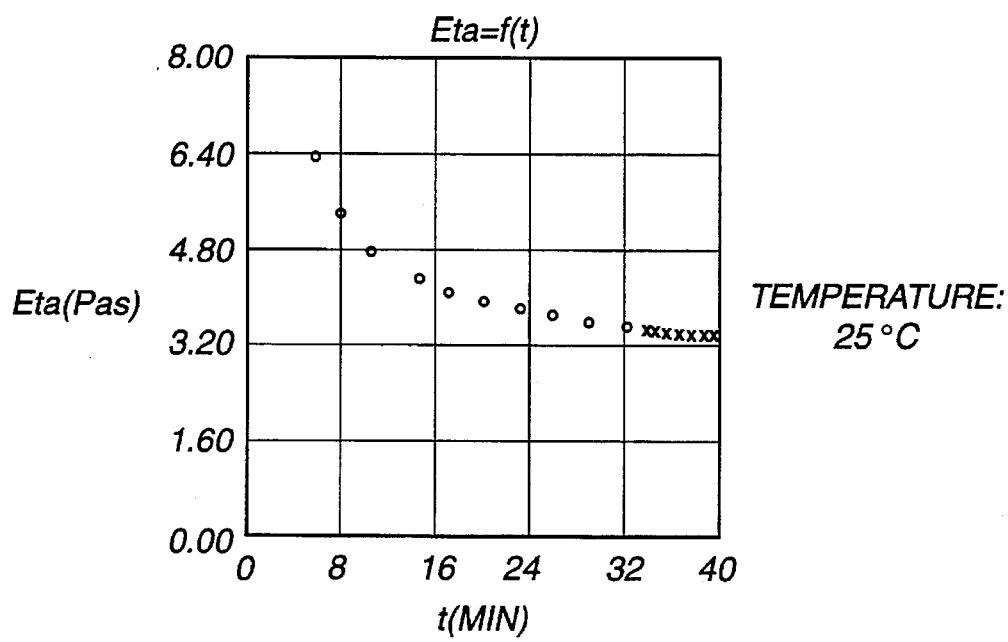
FIG. 3 CREAM OF EXAMPLE 2 VISCOSITY AT 25 °C
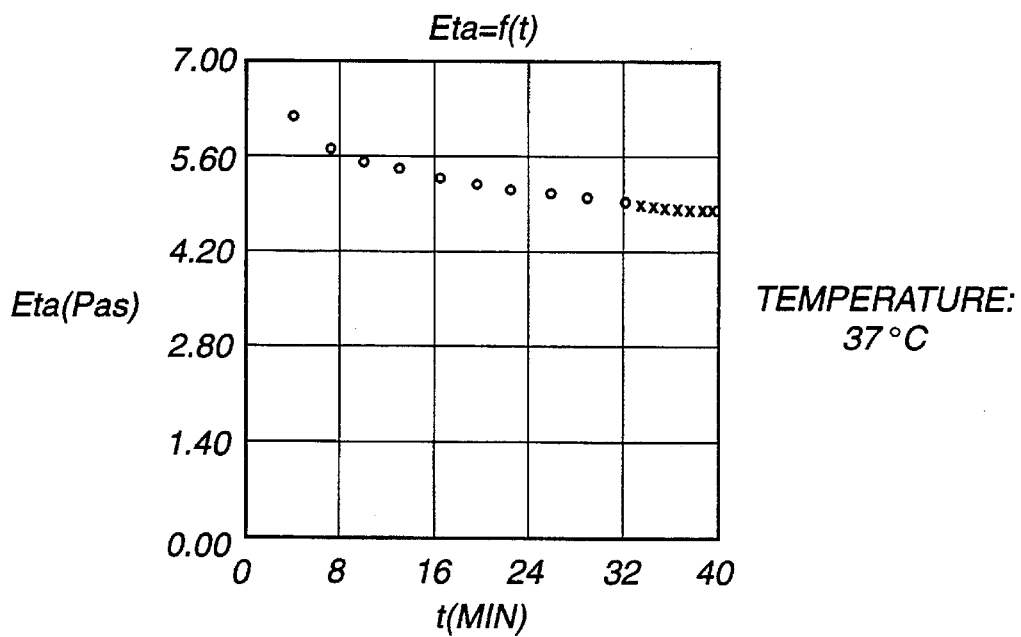
FIG. 4 CREAM OF EXAMPLE 2 VISCOSITY AT 37 °C

**CREAM I
VISCOSITY AT 25 °C**

TEMPERATURE: 25 °C

**CREAM I
VISCOSITY AT 37 °C**

TEMPERATURE: 37 °C

CREAM II VISCOSITY AT 25 °C

TEMPERATURE: 25 °C

CREAM II VISCOSITY AT 37 °C

TEMPERATURE: 37 °C

CREAM III VISCOSITY AT 25°C

TEMPERATURE: 25°C

CREAM III VISCOSITY AT 37°C

TEMPERATURE: 37°C

FIG. 11 CREAM OF EXAMPLE I
VISCOSITY PLOT FOR EXPERIMENT 3
(FROM 32 MINUTES TO 40 MINUTES TEMPERATURE IS RAISED
FROM 25 °C TO 37 °C)
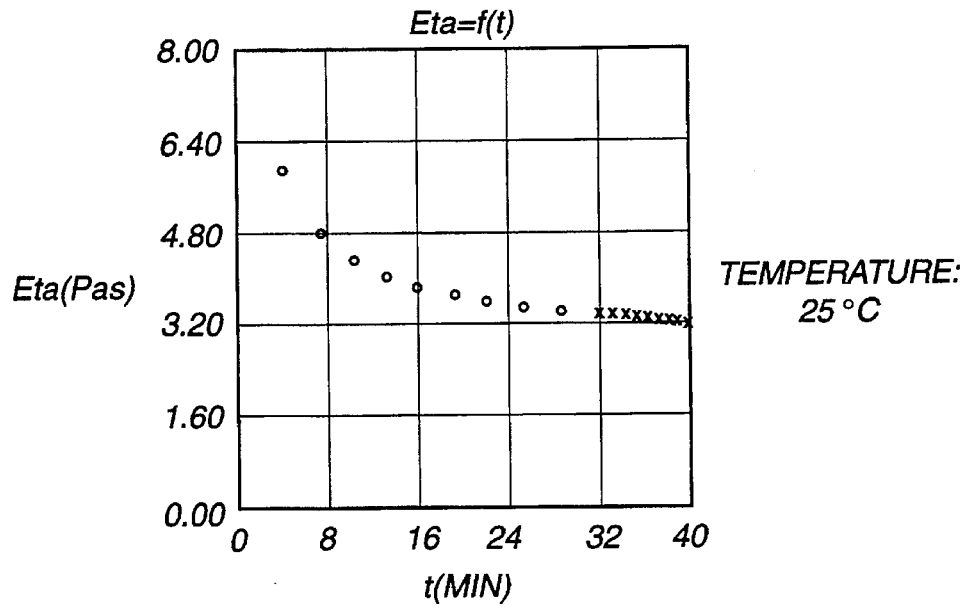
FIG. 12 CREAM OF EXAMPLE I
VISCOSITY PLOT FOR EXPERIMENT 3
(FROM 32 MINUTES TO 40 MINUTES TEMPERATURE IS RAISED
FROM 25 °C TO 37 °C)
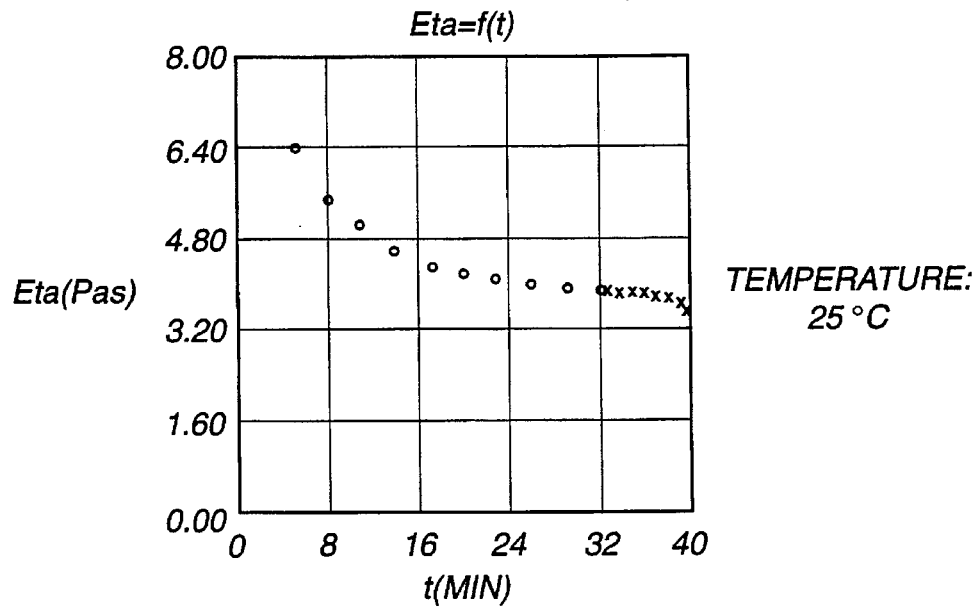

CREAM I
VISCOSITY PLOT FOR EXPERIMENT 3
*(FROM 32 MINUTES TO 40 MINUTES TEMPERATURE IS RAISED FROM 25 °C TO 37 °C)*

TEMPERATURE: 25 °C

CREAM OF EXAMPLE I
VISCOSITY PLOT FOR EXPERIMENT 3
*(FROM 32 MINUTES TO 40 MINUTES TEMPERATURE IS RAISED FROM 25 °C TO 37 °C)*

TEMPERATURE: 25 °C

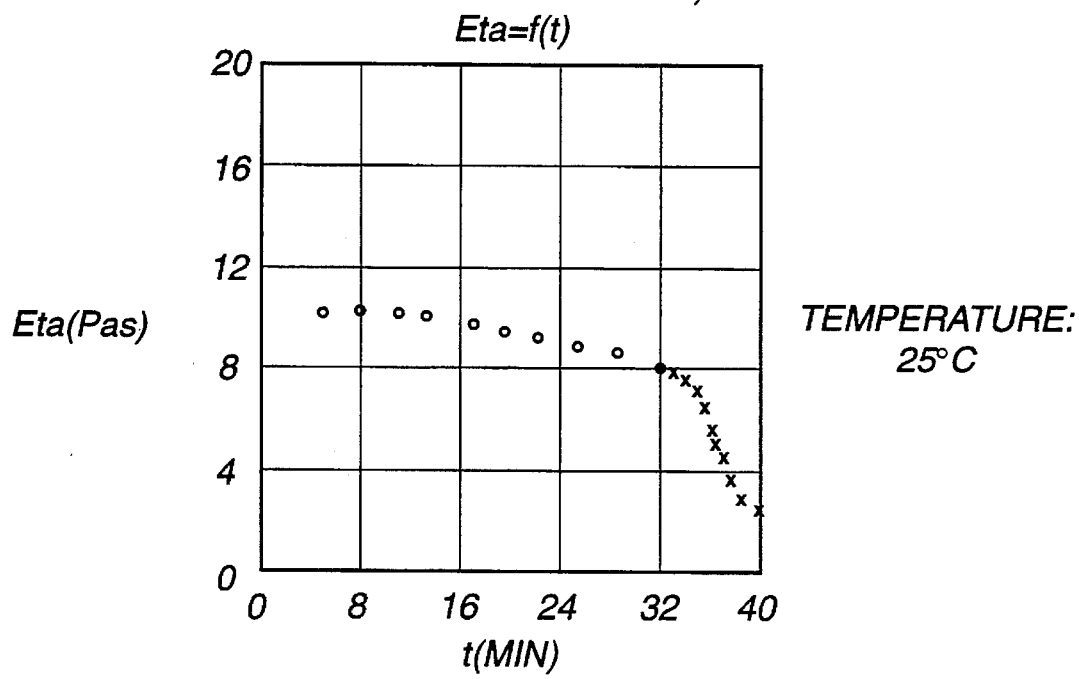
FIG. 15 CREAM OF EXAMPLE III
VISCOSITY PLOT FOR EXPERIMENT 3
(FROM 32 MINUTES TO 40 MINUTES TEMPERATURE IS RAISED FROM 25°C TO 37°C)
TEMPERATURE: 25°C

// 1

ANTIFUNGAL VAGINAL CREAM COMPOSITION

FIELD OF THE INVENTION

This invention relates to vaginal cream compositions containing antifungal compounds. More particularly, this invention relates to antifungal vaginal cream compositions which maintain viscosity at human body temperature.

BACKGROUND OF THE INVENTION

Conventional vaginal creams decrease in viscosity at human body temperature and, as a result, liquefy and exude from the vaginal cavity. The unwanted loss of cream diminishes the effectiveness of treatment and users may then be forced to seek further, more costly curative measures.

Accordingly, there is a need for a cream composition which will remain in the vaginal cavity for a longer duration than conventional cream compositions, thereby providing a user with an efficient treatment regimen.

SUMMARY OF THE INVENTION

The present invention now provides a long-lasting, viscous antifungal vaginal cream composition comprising about 0.4% to 10.0% of an antifungal agent; about 1.0% to 5.0% of a fatty acid ester; about 1.0% to 25.0% of aliphatic alcohols; about 2.0 to 5.0% of a surfactant; about 0.02% to 0.20% of an antioxidant; a sufficient amount of inorganic base to adjust the pH range to a value of about 3.0 to 7.0 and water.

Unlike conventional vaginal creams, the unique composition of the present invention is able to maintain viscosity for a prolonged time at human body temperature.

BRIEF DESCRIPTION OF THE FIGURES

FIG. 1 is a graph showing a plot of the viscosity of the miconazole nitrate cream formulation of Example 1 at 25° C.

FIG. 2 is a graph showing a plot of the viscosity of the miconazole nitrate cream formulation of Example 1 at 37° C.

FIG. 3 is a graph showing a plot of the viscosity of the miconazole nitrate cream formulation of Example 2 at 25° C.

FIG. 4 is a graph showing a plot of the viscosity of the miconazole nitrate cream formulation of Example 2 at 37° C.

FIG. 11 is a graph showing a plot of the viscosity of the miconazole nitrate cream formulation of Example 1 as the temperature is raised from 25° C. to 37° C.

FIG. 12 is a graph showing a plot of the viscosity of the miconazole nitrate cream formulation of Example 2 as the temperature is raised from 25° C. to 37° C.

FIG. 15 is a graph showing a plot of the viscosity of the state of the art Cream III as the temperature is raised from 25° C. to 37° C.

DETAILED DESCRIPTION OF THE INVENTION

Figure 5:
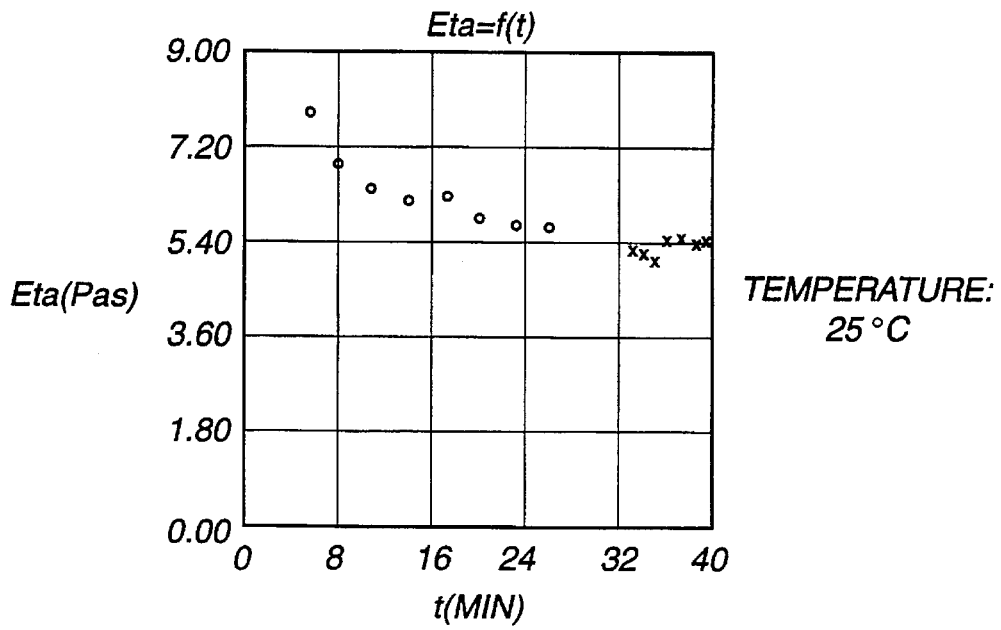
FIG. 5 is a graph showing a plot of the viscosity of the state of art Cream I at 25° C.
Figure 6:
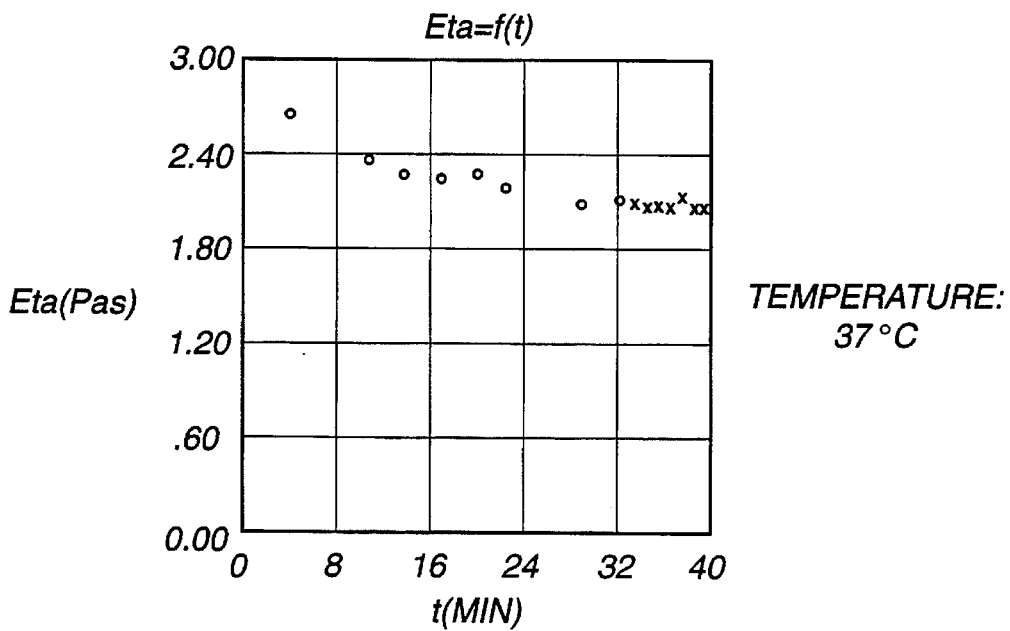
FIG. 6 is a graph showing a plot of the viscosity of the state of art Cream I at 37° C.
Figure 7:
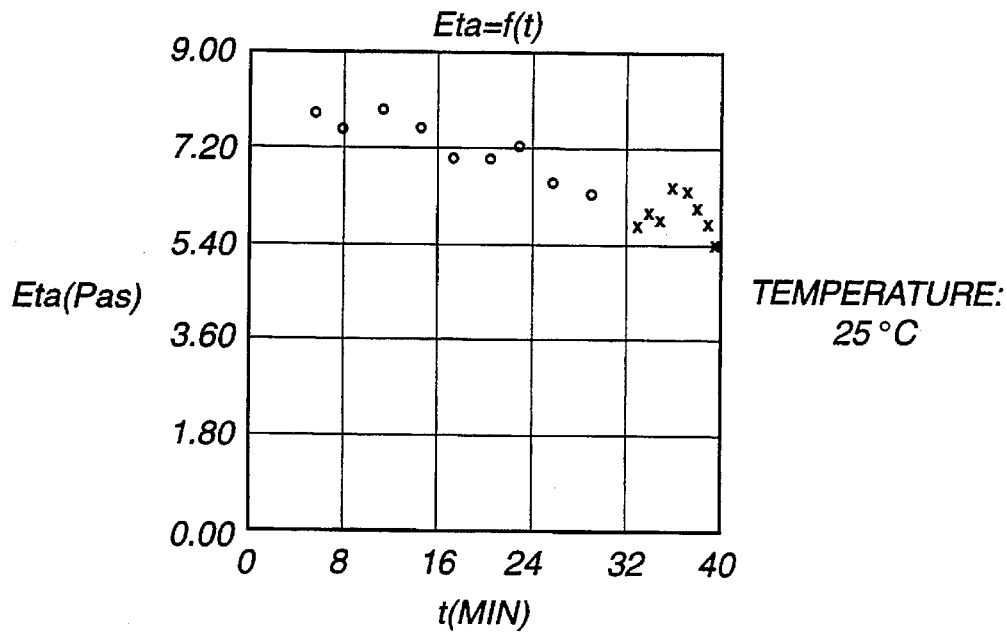
FIG. 7 is a graph showing a plot of the viscosity of the state of art Cream II at 25° C.
Figure 8:
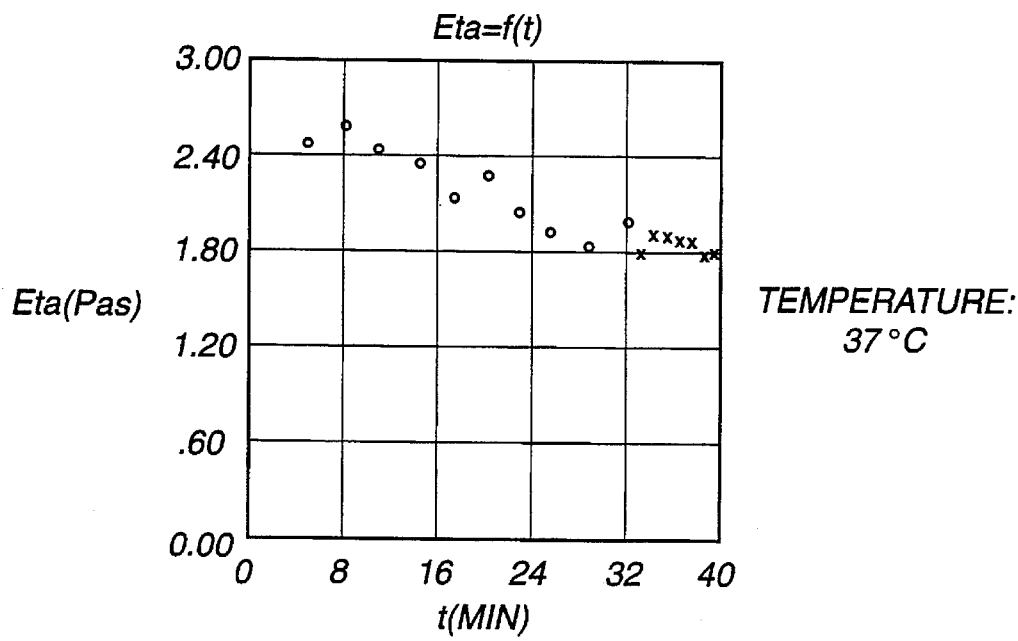
FIG. 8 is a graph showing a plot of the viscosity of the state of art Cream II at 37° C.
Figure 9:
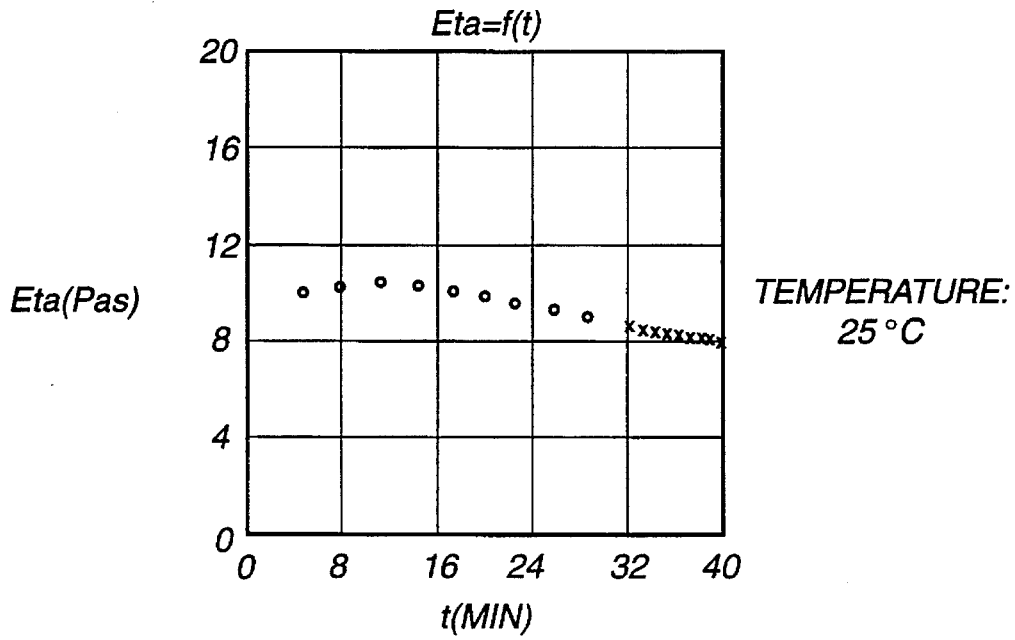
FIG. 9 is a graph showing a plot of the viscosity of the state of art Cream III at 25° C.
Figure 10:
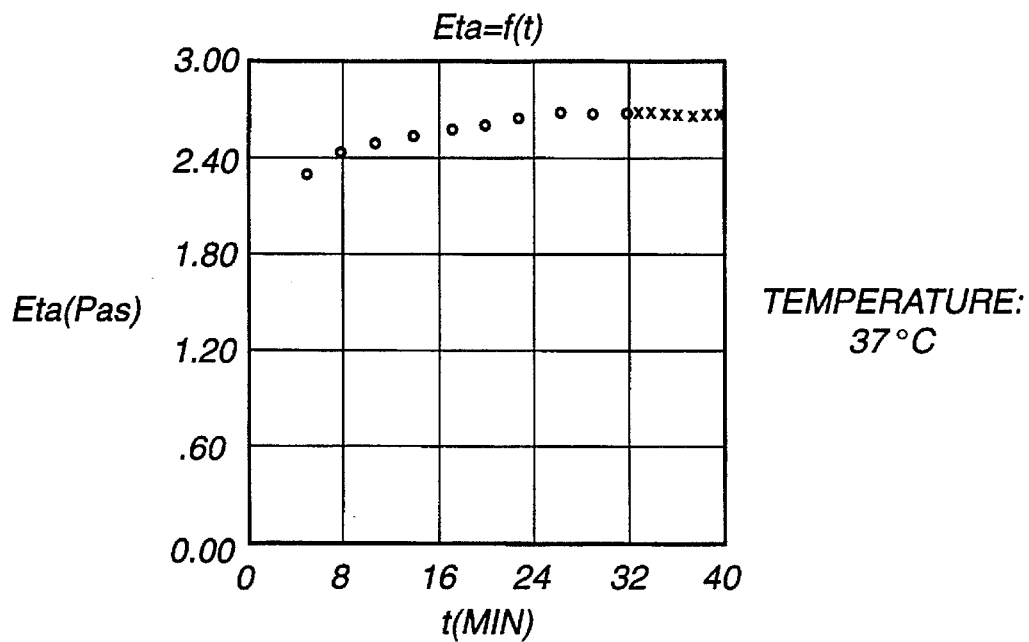
FIG. 10 is a graph showing a plot of the viscosity of the state of art Cream III at 37° C.
Figure 13:
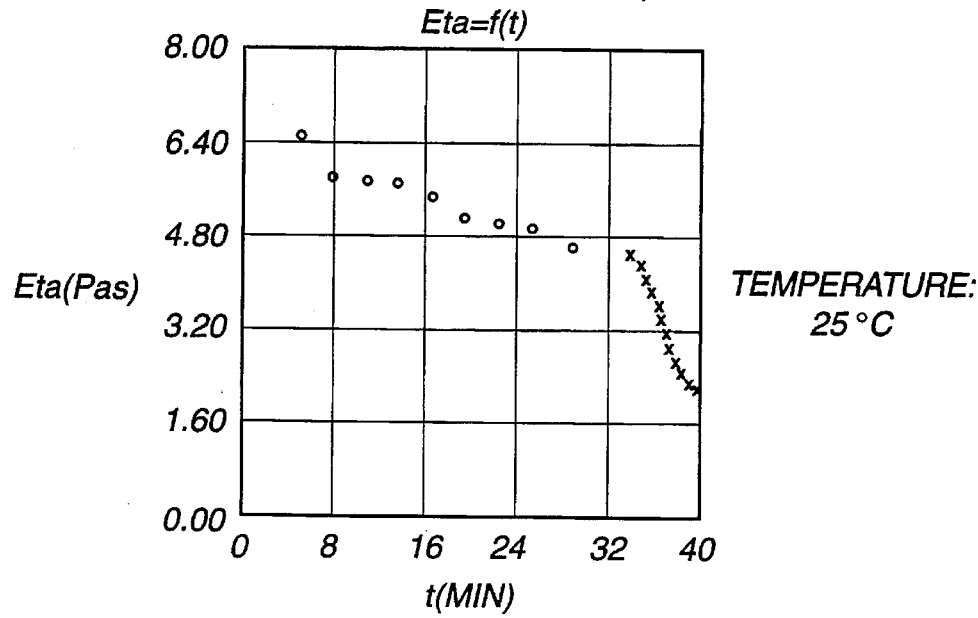
FIG. 13 is a graph showing a plot of the viscosity of the state of the art Cream I as the temperature is raised from 25° C. to 37° C.
Figure 14:
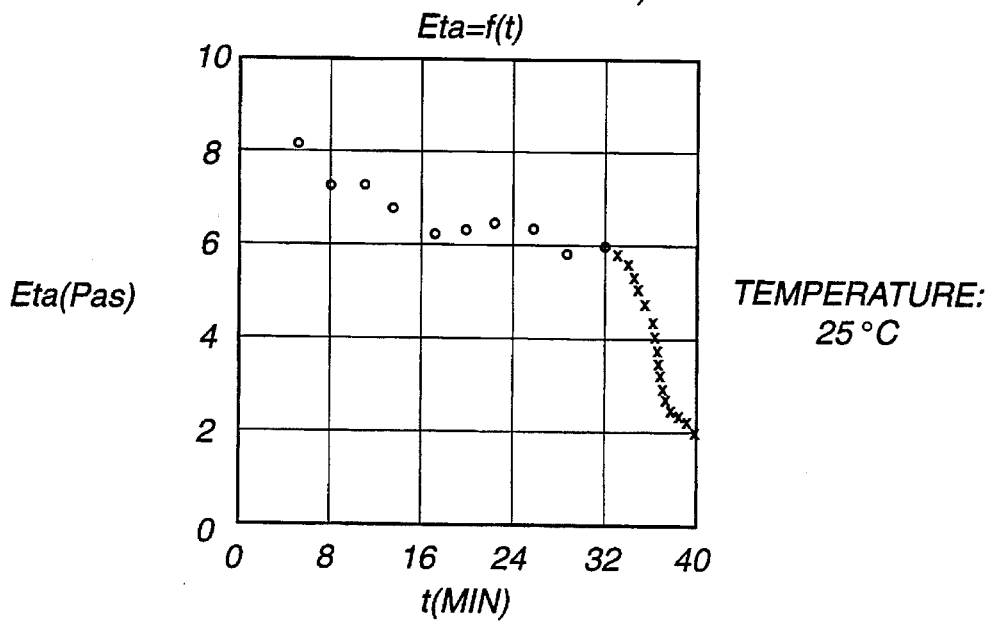
FIG. 14 is a graph showing a plot of the viscosity of the state of the art Cream II as the temperature is raised from 25° C. to 37° C.

The viscosity of conventional vaginal cream compositions decreases by about 70% to 80% at human body temperature, which is 37° C. Due to the loss in viscosity, the conventional creams liquefy and exude from the vaginal cavity. The unique composition of the vaginal cream of the present invention maintains a high viscosity even when the temperature of the cream is raised to 37° C.

According to one embodiment of the present invention, there is provided a viscous antifungal vaginal cream composition comprising aliphatic alcohols, an ester which is preferably a fatty acid ester, a surfactant, an inorganic base, an imidazole which acts as a vaginal antifungal, a substituted methoxyphenol which acts as an antioxidant, and water. The imidazole antifungal preferably is selected from the group consisting of miconazole, econazole, terconazole, ketoconazole, saperconazole, itraconazole, clotrimazole, tioconazole, butaconazole or other imidazoles.

The cream composition of the present invention is an oil in water (O/W) emulsion in which the oil phase is considered the internal or dispersed phase while the aqueous phase is considered the external or continuous phase. The oil phase of the composition preferably comprises cetyl alcohol, stearyl alcohol and isopropyl palmitate while the aqueous phase preferably comprises propylene glycol, butylated hydroxyanisole, potassium hydroxide and water. An antifungal compound, which is insoluble, is uniformly dispersed throughout the cream after the cream is formed.

A mixture of cetyl and stearyl alcohols, which act as auxiliary emulsifiers, impart to the oil phase of the cream an HLB (hydrophilic hydrophobic balance) value of about 15.2.

An ester, which acts as an emollient and lubricant, is included in the composition. The ester preferably is a fatty acid ester and is selected from the group consisting of isopropyl stearate, isopropyl myristate, isopropyl palmitate and isopropyl laurate. Most preferably, the ester is isopropyl myri-state. The ester provides the cream with smoothness and lubricity which, in turn, facilitate the loading of the cream into and dispensing of the cream from a vaginal applicator.

Preferably, propylene glycol is included as a humectant to prevent the cream from drying out and forming a crust. The humectant also improves the cream's consistency and spreadability, enhances solubility of the antifungal and acts as an antimicrobial agent.

Either polysorbate 60 or polysorbate 80 is included as a surfactant. The surfactant efficiently emulsifies the cream and imparts a high and stable viscosity even at a temperature of 37° C. when used at a preferred concentration of about 3.0% to 4.0%. Unlike the commercially available state of the art creams, the present composition does not require the use of two surfactants. One surfactant alone, having an HLB of 15.0 (which is close to the HLB value of the oil phase of the composition) has been found to impart to the cream its novel long-lasting viscous characteristics.

The composition further comprises a substituted methoxyphenol, preferably butyl hydroxyanisole, which acts as an antioxidant.

In preparing the viscous, antifungal vaginal cream composition of the present invention, the following amounts by weight of the total composition are preferably used:

| | |
|---|---|
| cetyl alcohol | 1.0%–7.0% |
| stearyl alcohol | 5.0%–15.0% |
| isopropyl myristate | 1.0%–5.0% |
| propylene glycol | 10.0%–25.0% |
| polysorbate 60 or 80 | 1.0%–5.0% |
| butylated hydroxyanisole | 0.02%–0.20% |
| antifungal compound | 0.4%–10.0% |
| sodium or potassium hydroxide | sufficient to adjust pH between 3–7 |
| Water | sufficient to make 100% |

The ranges given above impart to the cream composition a viscosity that is maintained at a temperature of at least 37° C. Each component is used in an amount necessary to be effective.

EXAMPLES

The invention is illustrated by the following examples which are not intended to be limitative thereof. All starting materials and reagents are commercially available from sources known to those skilled in the art, such as chemical supply houses.

Example 1

| | |
|---|---|
| Cetyl Alcohol | 3.00% |
| Stearyl Alcohol | 8.50% |
| Isopropyl Myristate | 1.00% |
| Propylene Glycol | 20.00% |
| Polysorbate 60 | 3.00% |
| Miconazole Nitrate | 2.00% |
| Potassium Hydroxide | 0.012% |
| Water q.s to | 100.000% |

The following manufacturing procedure is used: Cetyl alcohol, stearyl alcohol, isopropyl myristate and 2.8% polysorbate 60 are heated together to 75° C. in an appropriate container. In a separate container, water and propylene glycol are heated to 75° C. A portion of the water is saved for preparation of the miconazole nitrate slurry and preparation of sodium hydroxide solution. In a third container, water, 0.2% polysorbate 60 and miconazole nitrate are mixed to a slurry. In a fourth container, sodium hydroxide and water are mixed to a solution. When ready, the aqueous phase consisting of water and propylene glycol is added to the oil phase consisting of cetyl alcohol, stearyl alcohol, isopropyl myristate and polysorbate 60. Both phases are mixed and cooled to 40° C. and the miconazole slurry is added followed by the sodium hydroxide solution. The cream is mixed and cooled to 25° C. and passed through a homogenizer.

The viscosity of the composition of Example 1 was measured in accordance with the procedure set forth in Experiments 1 to 3.

Examples 2–16

The following examples are prepared in accordance with the manufacturing procedure of Example 1, utilizing the following formulations:

Example 2

| | |
|---|---|
| Cetyl Alcohol | 3.00% |
| Stearyl Alcohol | 8.50% |
| Isopropyl Myristate | 1.00% |
| Propylene Glycol | 20.00% |
| Polysorbate 60 | 3.00% |
| Miconazole Nitrate | 2.40% |
| Potassium Hydroxide | 0.012% |
| Water q.s to | 100.000% |

The viscosity of the composition of Example 2 was measured in accordance with the procedure set forth in Experiments 1 to 3.

Example 3

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 3.00% |
| Miconazole Nitrate | 2.00% |
| Potassium Hydroxide | 0.012% |
| Water q.s to | 100.00% |

Example 4

| | |
|---|---|
| Cetyl Alcohol | 3.00% |
| Stearyl Alcohol | 8.50% |
| Isopropyl Myristate | 1.00% |
| Butylated Hydroxyanisole | 0.025 |
| Propylene Glycol | 20.00% |
| Polysorbate 60 | 1.50% |
| Polysorbate 80 | 0.100% |
| Miconazole Nitrate | 2.00% |
| Potassium Hydroxide | 0.012% |
| Water q.s to | 100.00% |

Example 5

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 4.00% |
| Miconazole Nitrate | 2.00% |
| Potassium Hydroxide | 0.012% |
| Water q.s to | 100.000% |

Example 6

| | |
|---|---|
| Cetyl Alcohol | 3.00% |
| Stearyl Alcohol | 8.50% |
| Isopropyl Myristate | 1.00% |
| Butylated Hydroxyanisole | 0.025 |
| Propylene Glycol | 20.00% |
| Polysorbate 60 | 5.00% |
| Miconazole Nitrate | 2.00% |
| Potassium Hydroxide | 0.012% |
| Water q.s to | 100.00% |

Example 7

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00% |
| Miconazole Nitrate | 2.00% |
| Potassium Hydroxide | 0.012% |
| Water q.s to | 100.00% |

Example 8

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00% |
| Clotrimazole | 2.00% |
| Potassium Hydroxide | 0.012% |
| Water q.s to | 100.00% |

Example 9

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00% |
| Econazole | 1.00% |
| Potassium Hydroxide | 0.012% |
| Water q.s to | 100.00% |

Example 10

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00% |
| Itraconazole | 2.00% |
| Potassium Hydroxide | 0.012% |
| Water q.s to | 100.00% |

Example 11

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00% |
| Saperconazole | 2.00% |
| Potassium Hydroxide | 0.012% |
| Water q.s to | 100.00% |

Example 12

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00% |
| Terconazole | 0.40% |
| Potassium Hydroxide | 0.012% |
| Water q.s to | 100.00% |

Example 13

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00% |
| Terconazole | 0.80% |
| Potassium Hydroxide | 0.012% |
| Water q.s to | 100.00% |

Example 14

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00% |
| Ketoconazole | 2.00% |
| Potassium Hydroxide | 0.012% |
| Water q.s to | 100.00% |

Example 15

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.004 |
| Polysorbate 60 | 2.00% |
| Tioconazole | 2.00% |
| Potassium Hydroxide | 0.012% |
| Water q.s to | 100.00% |

Example 16

| | |
|---|---|
| Cetyl Alcohol | 3.00% |
| Stearyl Alcohol | 8.50% |
| Isopropyl Myristate | 1.00% |
| Butylated Hydroxyanisole | 0.025% |
| Propylene Glycol | 20.00% |
| Polysorbate 60 | 2.00* |
| Butaconazole | 2.00% |
| Potassium Hydroxide | 0.012% |
| Water q.s to | 100.00% |

Method of Viscosity Determination

The Haake VT 500 Rheometer is known to be a good instrument for testing viscosities of creams. The instrument is versatile and is able to run customized viscosity measurement programs.

Viscosity of the cream composition of the present invention was determined by the Haake VT 500 Rheometer Coaxial Cylinder Sensor System. The Haake F3 thermoregulating circulation pump was used with the rheometer to regulate the temperature of cream samples. To generate a computer printout of all data and to plot viscosity versus time, the IBM PC Computer, Haake Rheometer Software and Paint-Jet Laser Printer were used. Temperature was varied in order to study the effect of temperature on viscosity.

State of the art creams which are currently on the market are illustrated by the following compositions:

| State of the Art Cream I | |
|---|---|
| Gyne-Lotrimine ® (Schering-Plough) | |
| Clotrimazole | 1.000% |
| Benzyl Alcohol | |
| Cetearyl Alcohol | |
| Cetyl Esters Wax | |
| Octyldodecanol | |
| Polysorbate 60 | |
| Purified Water | |
| Sorbitan Monostearate | |
| Water q.s. to | 100.000% |

| State of the Art Cream II | |
|---|---|
| Fem Care ™ (Schering-Plough) | |
| Clotrimazole | 1.000% |
| Benzyl Alcohol | |
| Cetearyl Alcohol | |
| Cetyl Esters Wax | |
| Octyldodecanol | |
| Polysorbate 60 | |
| Purified Water | |
| Sorbitan Monostearate | |
| Water q.s. to | 100.000% |

| State of the Art Cream III | |
|---|---|
| Monistat ®7 (Advanced Care | |
| Products-Ortho Pharmaceutical Corp.) | |
| Benzoic Acid | 0.2000 |
| Butylated Hydroxyanisole | 0.0052 |
| Miconazole Nitrate | 2.0000 |
| Mineral Oil | 3.0000 |
| Peglicol 5 Oleate | 3.0000 |
| Pegoxol 7 Stearate | 20.0000 |
| Water q.s. to | 100.0000 |

| State of the Art Cream IV | |
|---|---|
| Albertsons ® Miconazole 7 | |
| Benzoic Acid | |
| Butylated Hydroxyanisole | |
| Miconazole Nitrate | 2.0000 |
| Glyceryl Monostearate | |
| Peglicol 5 Oleate | |
| Pegoxol 7 Stearate | |
| Water q.s. to | 100.0000 |

| State of the Art Cream V | |
|---|---|
| Miconazole 7 (Osco) | |
| Benzoic Acid | |
| Butylated Hydroxyanisole | |
| Miconazole Nitrate | 2.0000 |
| Glyceryl Monostearate | |
| Peglicol 5 Oleate | |
| Pegoxol 7 Stearate | |
| Water q.s. to | 100.0000 |

The following three viscosity measurement experiments were conducted. Temperature was varied in order to study the effect of temperature on viscosity.

Experiment 1 (Viscosity at 25° C.)

Cream samples were subjected to a constant shear and viscosity was measured for a period of 40 minutes. For the first two minutes, the sample was maintained at 25° C. without shear to stabilize the sample temperature.

The results of Experiment 1 are summarized in Tables I through V.

Experiment 2 (Viscosity with Temperature Raised to 37° C.)

For the first 32 minutes, the viscosity versus time experiment was run as in Experiment 1. For the remaining eight minutes, the viscosity was measured while the temperature of the sample was gradually raised to 37° C. The shear rate was maintained as in Experiment 1.

The results of Experiment 2 are summarized in Tables I through V.

Experiment 3 (Viscosity at 37° C.)

Viscosity was measured as in Experiment 1 except that the sample temperature was maintained at 37° C. throughout the experiment. This experiment demonstrated the behavior of the cream at human body temperature.

The results of Experiment 3 are summarized in Table VI.

Results

The viscosity of the creams of the present invention set forth in Examples 1 and 2 was measured according to the above Experiments. The viscosities of three commercially available vaginal creams, that is, state of the art Cream I, Cream II and Cream III, were also tested using the above Experiments. The data is summarized in Tables I through VI.

TABLE I

Cream of Example 1

| Time (minutes) | Viscosity Eta[Pas] 25° C. | Viscosity Eta [Pas] 37° C. |
|---|---|---|
| 5.2 | 4.9490 | 5.9390 |
| 10.0 | 4.9900 | 5.5200 |
| 15.4 | 3.6800 | 5.2790 |
| 20.2 | 3.4770 | 5.2030 |
| 25.00 | 3.3630 | 5.1020 |
| 30.40 | 3.2610 | 5.0000 |
| 35.14 | 3.2490 | 4.9750 |
| 40.00 | 3.1980 | 4.9620 |

TABLE II

Cream of Example 2

| Time (minutes) | Viscosity Eta[Pas] 25° C. | Viscosity Eta [Pas] 37° C. |
|---|---|---|
| 5.00 | 7.1194 | 6.4088 |
| 10.40 | 5.5204 | 5.8250 |
| 15.20 | 4.8732 | 5.7615 |
| 20.00 | 4.1579 | 5.5966 |
| 25.40 | 4.2764 | 5.5585 |
| 30.20 | 4.1244 | 5.5077 |
| 35.04 | 3.9849 | 5.4950 |
| 40.00 | 3.8706 | 5.4062 |

Results of State of the Art Creams I, II and III

TABLE III

Cream I Gyne-Lotrimin ®

| Time (minutes) | Viscosity Eta[Pas] 25° C. | Viscosity Eta [Pas] 37° C. |
|---|---|---|
| 5.00 | 7.8809 | 2.6413 |
| 10.40 | 6.7006 | 2.2716 |
| 15.20 | 6.2438 | 2.2843 |
| 20.00 | 5.9900 | 2.2843 |
| 25.40 | 5.5458 | 1.9163 |
| 30.20 | 5.6092 | 2.0432 |
| 35.04 | 5.6727 | 2.1066 |
| 40.00 | 5.6092 | 2.1066 |

TABLE IV

Cream II Fem Care ™

| Time (minutes) | Viscosity Eta[Pas] 25° C. | Viscosity Eta [Pas] 37° C. |
|---|---|---|
| 5.00 | 8.1347 | 2.5127 |
| 10.40 | 7.7413 | 2.4366 |
| 15.20 | 7.5382 | 2.2843 |
| 20.00 | 7.0814 | 2.2589 |
| 25.40 | 6.9292 | 2.0432 |
| 30.20 | 6.3453 | 1.9290 |
| 35.04 | 6.0153 | 1.8274 |
| 40.00 | 5.4062 | 1.7894 |

TABLE V

Cream III Monistat ®7

| Time (minutes) | Viscosity Eta[Pas] 25° C. | Viscosity Eta [Pas] 37° C. |
|---|---|---|
| 5.00 | 10.0002 | 2.3351 |
| 10.40 | 10.2667 | 2.4747 |
| 15.20 | 10.0002 | 2.5762 |
| 20.00 | 9.7337 | 2.6016 |
| 25.40 | 9.3276 | 2.6270 |
| 30.20 | 8.8327 | 2.6396 |
| 35.04 | 3.2490 | 2.6904 |
| 40.00 | 7.9570 | 2.6777 |

TABLE VI

| Viscosity Creams | Viscosity Eta[Pas] Cream of this Invention | | Viscosity Eta[PAS] State of the Art Creams | | |
|---|---|---|---|---|---|
| | Example 1 | Example 2 | Cream I | Cream II | Cream III |
| Viscosity after 32 minutes at 25° C. | 3.3630 | 3.879 | 4.7336 | 6.0788 | 8.1601 |
| Viscosity after 8 minutes at 37° C. | 3.1090 | 3.4645 | 1.9924 | 1.8655 | 2.3605 |

The results of Experiments 1 and 2 are summarized in Tables I through V. The data show that at the end of 40 minutes, the viscosity at 37° C. for the creams of Example 1 and 2 (Tables I and II) of the present invention are 55% and 40% higher when compared to their respective viscosities at 25° C. The viscosities of the state of the art Creams I, II, III (Tables III, VI and V) at the end of 40 minutes are 62%, 67% and 66% lower at 37° C. as compared to their viscosities at 25° C.

The results of Experiment 3 (Table VI) in which, during the last eight (8) minutes of the experiment the temperature of the creams was gradually raised from 25° C. to 37° C., confirm the results of Experiments 1 and 2. When the temperature was raised from 25° C. to 37° C. in eight (8) minutes, the viscosities of the creams of Examples 1 and 2 decrease by only 7.6% and 10.7%, while viscosities of the state of the art Creams I, II, and III decrease by 57.9%, 69.3% and 71.1% respectively. These results make the creams of the present invention very unique.

Examples 1 and 2 represent the preferred embodiments of the composition. The scope of the current invention, however, is not limited to these examples. Those skilled in the art will recognize or be able to ascertain, using no more than routine experimentation, many equivalents to the specific embodiments of the invention described herein. Such equivalents are intended to be encompassed in the scope of the following claims.

What is claimed is:

1. A long-lasting viscous antifungal vaginal cream composition comprising about 0.4 to 10.0% of an imidazole antifungal agent; about 1.0% to 5.0% of a fatty acid ester; about 1.0% to 25.0% of aliphatic alcohols; about 2.0% to 5.0% of a surfactant; about 0.02% to 0.20% of an antioxidant; a sufficient amount of inorganic base to adjust the pH range to a value of about 3.0 to 7.0 and water, said composition maintaining its viscosity when the temperature of the cream is raised to 37° C.

2. The composition according to claim 1 wherein the imidazole is selected from the group consisting of miconazole, econazole, terconazole, saperconazole, itraconazole, ketoconazole, and clotrimazole.

3. The composition according to claim 1 wherein the ester is selected from the group consisting of isopropyl stearate, isopropyl myristate, isopropyl palmitate, and isopropyl laurate.

4. The composition according to claim 1 wherein the aliphatic alcohols are selected from the group consisting of cetyl alcohol, stearyl alcohol and propylene glycol.

5. The composition according to claim 1 wherein the surfactant is polysorbate 60 or polysorbate 80.

6. The composition according to claim 5 wherein the surfactant has an HLB value of about 15.

7. The composition according to claim 1 wherein the antioxidant is butylated hydroxyanisole.

8. The composition according to claim 1 wherein the inorganic base is sodium hydroxide.

9. The composition according to claim 1 wherein the inorganic base is potassium hydroxide.

10. A long-lasting viscous antifungal vaginal cream composition according to claim 1 wherein said cream has a viscosity of at least about 3.1 Eta (Pas) at 37° C. after at least eight minutes.

11. A long-lasting viscous antifungal vaginal cream composition according to claim 1 wherein said cream has a viscosity which decreases by no more than about 10 percent at 37° C. after at least eight minutes.

12. A method for making a long-lasting viscous antifungal vaginal cream composition comprising the following steps:

(a) mixing an oil phase comprising an aliphatic alcohol, an ester and a surfactant;

(b) separately mixing an aqueous phase comprising water and a humectant;

(c) separately, mixing surfactant, water and an antifungal agent and creating a slurry;

(d) separately mixing an alkaline buffer compound and water;

(e) adding said aqueous phase to said oil phase, mixing and cooling the resulting mixture;

(f) after step (e), adding said slurry to the resulting mixture; and (g) adding the alkaline buffer compound and water mixture to adjust the pH of the resulting mixture.

13. A method according to claim 12 wherein said antifungal agent is selected from the group consisting of miconazole, econazole, terconazole, sperconazole, itraconazole, ketoconazole, and clotrimazole.

14. A method according to claim 12 wherein said ester is selected from the group consisting of isopropyl stearate, isopropyl myristate, isopropyl palmitate, and isopropyl laurate.

15. A method according to claim 12, wherein said aliphatic alcohol is selected from the group consisting of cetyl alcohol, stearyl alcohol and propylene glycol and mixtures thereof.

16. A method according to claim 12 wherein said surfactant is polysorbate 60 or polysorbate 80.

17. A method according to claim 16 wherein said surfactant has an HLB value of about 15.

18. A long-lasting viscous antifungal vaginal cream composition made in accordance with the method of claim 12.

19. A long-lasting viscous antifungal vaginal cream composition comprising about 0.4 to 10.0% of an imidazole antifungal agent; about 1.0% to 5.0% of a fatty acid ester; about 1.0% to 25.0% of aliphatic alcohols; about 2.0% to 5.0% of a surfactant; about 0.02% to 0.20% of an antioxidant; a sufficient amount of inorganic base to adjust the pH range to a value of about 3.0 to 7.0 and water, said surfactant having an HLB which is close to the HLB value of the oil phase of the composition.

* * * * *